United States Patent [19]

Horrobin et al.

[11] Patent Number: 4,758,592

[45] Date of Patent: Jul. 19, 1988

[54] METHOD OF TREATING OR PREVENTING ENDOMETRIOSIS

[75] Inventors: David F. Horrobin, Guildford, England; Robert A. Casper, Ontario, Canada

[73] Assignee: Efamol Limited, Surrey, England

[21] Appl. No.: 911,719

[22] Filed: Sep. 26, 1986

[30] Foreign Application Priority Data

Oct. 2, 1985 [GB] United Kingdom ............... 8524276

[51] Int. Cl.$^4$ ..................... A61K 31/23; A61K 31/22
[52] U.S. Cl. .................................... 514/549; 514/560
[58] Field of Search ................... 514/560; 424/107, 95

[56] References Cited

U.S. PATENT DOCUMENTS 4,526,902  7/1985  Rubin .............................. 514/560

OTHER PUBLICATIONS

Chapter 22, "Endometriosis", James H. Evans and Ian Johnston, from *Clinical and Reproductive Endocrinology*, Shearman (editor), pp. 452–463, Churchill Livingstone Publishers.

*Primary Examiner*—Jerome D. Goldberg
*Assistant Examiner*—Richard Kearse
*Attorney, Agent, or Firm*—Nixon & Vanderhye

[57] ABSTRACT

Method of prevention or treatment of endometriosis wherein effective amounts of one or both of (i) gamma-linolenic acid and/or dihomo-gamma-linolenic acid and (ii) 18:4 n-3 and/or one or more of the metabolites of 18:4 n-3 (20:4 n-3, 20:5 n-3, 22:5 n-3 or 22:6 n-3) are administered against endometriosis as such or in the form of an ester, salt, amide or other derivative convertible in the body thereto, alone or in an acceptable pharmaceutical carrier or diluent.

3 Claims, No Drawings

METHOD OF TREATING OR PREVENTING ENDOMETRIOSIS

DESCRIPTION

1. Field of the Invention

This invention relates to the prevent or treatment of endometriosis.

2. General Background

The essential fatty acids (EFAs) are of two types, the n-3 (or omega-3) series derived from alpha-linolenic acid and the n-6 (or omega-6) series derived from linoleic acid. Linoleic acid and alpha-linolenic acid are like vitamins in that they cannot be manufactured in the body and therefore must be provided in the diet. The body can metabolise them along the pathways below and such metabolism is believed to be essential if they are to fulfil their functions. The pathways, sharing it is believed common enzymes, are:

| n-6 | | n-3 | |
|---|---|---|---|
| 18:2 | delta-9,12(linoleic acid) | 18:3 | delta-9,12,15(alpha-linolenic acid) |
| ↓ | delta-6 desaturase | ↓ | |
| 18:3 | delta-6,9,12(gamma-linolenic acid) | 18:4 | delta-6,9,12,15 |
| ↓ | elongation | ↓ | |
| 20:3 | delta-8,11,14(dihomo-gamma-linolenic acid) | 20:4 | delta-8,11,14,17 |
| ↓ | delta-5 desaturase | ↓ | |
| 20:4 | delta-5,8,11,14(arachidonic acid) | 20:5 | delta-5,8,11,14,17 |
| ↓ | elongation | ↓ | |
| 22:4 | delta-7,10,13,16(adrenic acid) | 22:5 | delta-7,10,13,16,19 |
| ↓ | delta-4 desaturase | ↓ | |
| 22:5 | delta-4,7,10,13,16 | 22:6 | delta-4,7,10,13,16,19 |

The pathways are not normally reversible nor, in man, are n-3 and n-6 series acid interconvertible.

The acids, which naturally are of the all-cis configuration, are systematically named as derivatives of the corresponding octadecanoic, eicosanoic or docosanoic acids, e.g. delta-9,12-octadecadienoic acid or delta-4,7,10,13,16,17-docosahexaenoic acid, but numerical designation such as, correspondingly, 18:2 n-6 or 22:6 n-3 is convenient. Initials, for example, DHA for 22:6 n-3 (docosahexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature is to the alpha-acid.

In the body, the n-3 acids are metabolised preferentially and as a result, in plasma for example, levels of alpha-linolenic acid (18:3 n-3) are low and 18:4 n-3 and 20:4 n-3 are in trace amounts only. In contrast the n-6 acids are normally present in moderate amounts, though gamma-linolenic acid (GLA) is at low levels, being apparently converted to dihomo-gamma-linolenic acid (DGLA) more rapidly than its relatively slow production from linoleic acid. In both series the elongation stages in the metabolic pathways are much more rapid than the desaturations.

Particular significance of the n-6 series acids lies in prostaglandin (PG) synthesis, the outline of which is believed to be as shown in the following diagram:

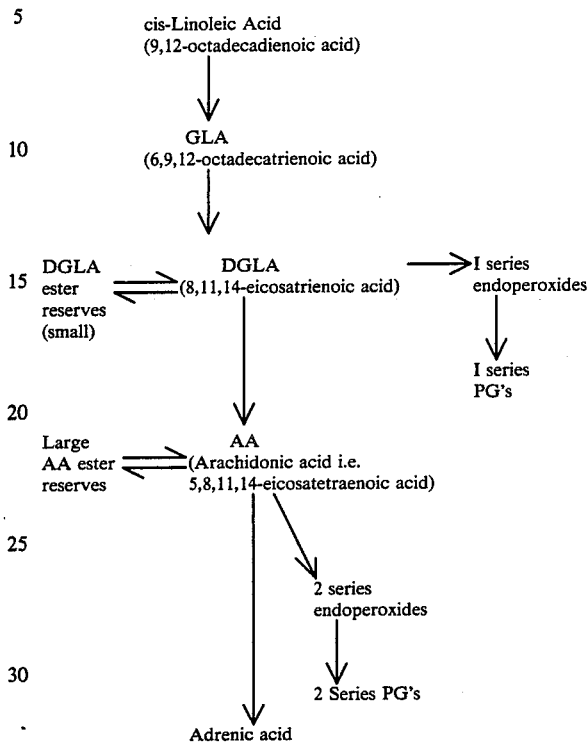

The broad outline of this pathway is well known, and it brings out clearly that a major function of essential fatty acids is to act as precursors for 1-series PGs formed from DGLA and 2-series PGs formed from arachiodonic acid. Further, it has recently been found that the 22:4 n-6 acid produced from arachiodonic acid gives rise to a series of homo-2-series PGs, though their importance is as yet unknown.

DGLA is the key substance. GLA is almost completely and very rapidly converted in the body to DLGA and so for practical purposes the oral administration of DGLA and GLA amounts to the same thing. DGLA can be converted to a storage for or to PGs of the 1-series, or through arachiodonic acid, to PGs of the 2-series.

Considering dietary requirements, it is well known, for example, that linoleic acid cannot be made by the body and so must be taken in the diet. However, it has been generally thought that the body can metabolise linoleic acid to all the other n-6 acids and therefore that provided linoleic acid intake is adequate, no lack of the other n-6 acids will be found.

In previous patent applications (for example Published European Patent Application No. A 0 003 407, U.S. Pat. No. 4,415,554; Published European Patent Application No. A 0 004 770, U.S. Pat. No. 4 309 415; Published European Patent Application No. 0 019 423, U.S. Pat. No. 4,388,324) it has, however, been pointed out that the first enzyme in the pathway, the delta-6 desaturase which, for example, converts linoleic acid to GLA, is not fully effective in a variety of conditions. The administration of GLA or DGLA or both has been suggested and has been successful in treating a variety of clinical conditions.

In the above patent applications attention is primarily paid to the function of essential fatty acids in prostaglandin metabolism and in particular to their role in securing a proper balance between 1-series and 2-series PGs. Attention is primarily paid therefore to the n-6 acids.

The applicants are, however, becoming increasing aware of the significance of the essential fatty acids in themselves as set out above. Considerable general interest has been shown in them in recent years, primarily in the acids of the n-6 series both as such and in relation to prostaglandin metabolism, but also in the acids of the n-3 series. The n-6 acids in particular are believed to be required in the body for the structure of membranes in and around cells, for maintaining normal flexibility, fluidity and permeability of such membranes and the n-3 acids are unlikely to have a more passive role.

Endometriosis is a common condition affecting women of reproductive age. For unknown reasons, endometrial tissue migrates from its normal position lining the uterus to other parts of the body, primarily within the abdominal cavity. The ovaries and gut wall are commonly affected. The endometrial tissue, like that in its normal position, grows and declines according to the menstrual cycle as a result of the actions of the ovarian hormones. Endometriosis causes many symptoms including abdominal and back pain, gastrointestinal upsets, infertility and menstrual disturbance. Since endometrial tissue requires ovarian hormones for growth, symptoms of endometriosis normally decline and disappear after the menopause. There is no satisfactory pre-menopausal treatment other than the use of drugs or other measures which suppress or remove ovarian functions or which antagonise the actions of ovarian hormones. Since such drugs interfere with fertility, they cannot be satisfactorily used in women whose main problem is infertility. Further, such drugs have many side effects and the suppression of normal reproductive function is unacceptable to many women.

It has previously been shown (unpublished European Patent Application No. 86304860.9, U.S. patent application Ser. No. 878,684, see also European Pat. No. B0003407, and U.S. Pat. No. 4,415,554) that GLA is effective in the treatment and prevention of premenstrual syndrome. It has also been found that in women with premenstrual syndrome there is evidence of restricted delta-6 desaturase activity. Many women with premenstrual syndrome respond to administration of GLA or the higher n-6 acids which by-passes the delta-6 desaturase step: some, but not all, seem to do even better when n-3 acids, for example from fish oil containing e.g. the 20:5 n-3 and 22:6 n-3 acids, are used in conjunction with the GLA, etc.

Some of the women with premenstrual syndrome also have endometriosis. Surprisingly, the inventors have found that in these women the administration of evening primrose oil (which contains GLA) produces a dramatic reduction in the symptoms of endometriosis, including the pain, gastrointestinal disturbances and menstrual distress. Combination of evening primrose oil with fish oil produces rather better results than the use of evening primrose oil alone, indicating that the fatty acids in the fish oil are making a contribution to the therapeutic effect. This treatment is a substantial development in the treatment of endometriosis, since the essential fatty acids do not interfere with fertility, so providing the first successful approach to this disease which does not even temporarily impair fertility.

The theoretical basis of the inventors' observations is unclear. Since most women in European and North America are taking plenty of linoleic acid and alpha-linolenic acid in the diet, the present findings suggest that there may be in these women with endometriosis a restricted conversion of linoleic acid to GLA and of alpha-linolenic acid to 18:4 n-3 and that this restricted conversion, in ways which are not yet understood, contributes to the symptoms of endometriosis. Although the inventors' observations relate directly only to GLA among the n-6 essential fatty acids, GLA is rapidly converted to DGLA and it is therefore likely the DGLA will also be of value. It is unlikely that the further metabolite, AA, will be helpful since some of the 2-series prostaglandins formed from it are known to be elevated in patients with endometriosis and in any case AA is rarely deficient in the diet. It is more likely that in endometriosis there is an imbalance between the substances including 1-series PGs derived from DGLA and those including 2-series PGs derived from AA, as discussed in detail in the Patent Applications referred to above to which reference may be made. The administration of GLA or DGLA helps to restore a normal PG balance. With the n-3 essential fatty acids, it is to be expected that 18:4 n-3, 20:4 n-3 and 22:5 n-3 will be of value, in addition to the demonstrated effects of administering 20:5 n-3 and 22:6 n-3 as the n-3 acids do not have a function in PG synthesis. None is plentiful in a standard diet and, with the restriction in delta-6 desaturase activity referred to above, they will not be produced in the normal way from dietary alpha-linolenic acid.

DETAILED STATEMENT OF INVENTION

In the light of the discussion above the present invention may be summarised as:

(i) A method of prevention or treatment of endometriosis wherein effective amounts of one or both of (i) GLA and/or DGLA and (ii) 18:4 n-3 and/or one or more of the metabolites of 18:4 n-3 (20:4 n-3, 20:5 n-3, 22:5 n-3 or 22:6 n-3) are administered against endometriosis as such or in the form of an ester, salt, amide or other derivative convertible in the body thereto, alone or in an acceptable pharmaceutical carrier or diluent.

(ii) Compositions of said acid or metabolites when for such use and the preparation of medicaments, being such compositions for such use.

All the acids may as noted be administered in the form of the acid itself or as an ester, amide, salt or any other functional derivative capable of being converted to the acid within the body and may be from natural or synthetic sources. Conversion of derivatives, of which glyceride esters such as those of GLA in evening primrose oil are the preferred form, is shown by their having the desirable effect in the body of the acids themselves or directly by analyses of plasma or other tissue by standard techniques, for example, those of Pelick et al. page 23, "Analysis of Lipids and Lipoproteins", Ed. Perkins, American Oil Chemists Society, Champaign, Ill. U.S.A.

Judging by their presence in various body tissues, the important n-3 essential fatty acids are 20:5 n-3 and 22:6 n-3. One therefore wants most preferably to use combinations of either 18:4 n-3 or 20:4 n-3 which can give rise to 20:5 n-3 and 22:6 n-3, or of those acids themselves, with either GLA or DGLA.

Doses for each acid are from 1 mg to 100 g per day, preferably 50 mg to 5 g per day, conveniently in conventional gelatine capsules.

PACKS

If it is not desired to have compositions comprising the different active materials together, packs may be prepared comprising the materials presented for separate, or part joint and part separate administration in the appropriate relative amounts, and use of such packs is within the purview of this invention.

FORMS AND SOURCES OF GAMMA-LINOLENIC AND OTHER ACIDS

Convenient physiologically equivalent derivatives of gamma-linolenic acid and dihomo-gamma-linolenic acid for use according to the invention, as with the other acids, include salts, amides, esters including glyceride esters and alkyl (e.g. $C_1$ to $C_4$) esters, and phospholipids. As noted above, reference to the acids in the claims and elsewhere herein are to be taken as including them when in the form of said derivatives.

If desired, pharmaceutical compositions may be produced for use in the invention by associating the natural or synthetic acids, as such or as derivatives, with an acceptable pharmaceutical vehicle. It is, however, at present convenient to incorporate at least the gamma-linolenic acid into compositions in the form of an available oil having a high gamma-linolenic acid content, hence reference to "oil" herein.

At the present time known natural sources of oils having a high gama-linolenic acid content are few (there are no known natural sources of significant amounts of dihomo-gamma-linolenic acid). One source of oils currently available is the seed of evening primrose species such as *Oenothera biennis L.* and *Oenothera Lamarckiana,* the oil extract therefrom containing gamma-linolenic acid (about 8%) and linoleic acid (about 72%) in the form of their glycerides together with other glycerides (percentages based on total fatty acids). Other sources of gamma-linolenic acid are Borage species such as *Borago officinalis* which, though current yield per acre is low, provide a richer source of gamma-linolenic acid then Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractination of a typical sample of this oil in the form of methyl esters shows the relative proportions:

Palmitate: 6.15
Stearate: 1.6
Oleate: 10.15
Linoleate: 72.6
Gamma-linolenate: 8.9

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

Natural sources of 22:4 and 22:5 n-6 acids include adrenal glands (22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

Advantageously, a preservative is incorporated into the preparations: alpha-tocopherol in concentration of about 0.1% by weight has been found suitable for the purpose.

DIETARY COMPOSITIONS

The invention is chiefly described in terms of use of pharmaceutical compositions, but it will be understood that the gamma-linolenic and other acids being in the nature of dietary supplements, could be incorporated in a dietary margarine or other foodstuffs: use of such foodstuffs, possibly containing other active materials and generally referred to in this description as dietary or pharmaceutical compositions, are within the purview of the invention and thus of the term pharmaceutical compositions or the like used in the claims.

VETERINARY APPLICATIONS

It will be understood that where a disorder of a kind calling for treatment in animals arises, the invention while described primarily in terms of human medicine and treatment is equally applicable in the veterinary field.

PHARMACEUTICAL PRESENTATION

The compositions used according to the invention are conveniently in a form suitable for oral, rectal, parenteral or topical administration in a suitable pharmaceutical vehicle, as discussed in detail for example in U.K. Patent Specification No. 1 082 624 and in any case very well known generally for any particular kind of preparation. Thus for example, tablets, capsules, ingestible liquid or powder preparations, creams and lotions for topical application, or suppositories, can be prepared as required. Injectable solutions of hydrolysed Oenothera oil may be prepared using albumin to solubilise the free acid.

Advantageously a preservative is incorporated into the preparations. Alpha-tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following are specific Examples of the invention against the symptoms of endometriosis.

EXAMPLE 1

A capsule containing 0.3 g evening primrose oil and 0.2 g mackerel oil administered six times per day.

EXAMPLE 2

A capsule containing 0.35 g evening primrose oil and 0.15 g salmon oil administered eight times per day.

EXAMPLE 3

A capsule containing 150 mg of GLA and 100 mg of 20:5 n-3 administered three times per day.

EXAMPLE 4

A capsule containing 50 mg of DGLA, 20 mg of 18:4 n-3, 20 mg of 20:4 n-3, 50 mg of 20:5 n-3, 20 mg of 22:5 n-3 and 20 mg of 22:6 n-3 taken four times per day.

EXAMPLE 5

A capsule containing 0.5 g evening primrose oil administered six times per day.

We claim:

1. A method of preventing or treating endometriosis comprising administering to a woman in need thereof effective amounts of one or both of i) gamma-linolenic acid, dihomo-gamma-linolenic acid or both or ii) stearidonic acid or one or more of the metabolites of stearidonic acid (delta-8,11,14,17- eicosatetraenoic acid, delta-5,8,11,14,17-eicosatetraenoic acid, delta-7,10,13,16,19-docosahexaenoic acid or delta-4,7,10,13,16,19-docosahexaenoic acid) as such or in the form of a pharmaceutically acceptable ester, salt, or amide, alone or in an acceptable pharmaceutical carrier or diluent.

2. A method as claimed in claim 1 wherein the amounts of each said acid are 1 mg to 100 g, or submultiples thereof, per unit dose.

3. A method as claimed in claim 1 wherein the amounts of each said acid are 50 mg to 5 g per day.

* * * * *